United States Patent [19]
Tsujita

[11] Patent Number: 5,541,515
[45] Date of Patent: Jul. 30, 1996

[54] MRI JOINT IMAGING SYSTEM

[75] Inventor: Kazuhiko Tsujita, Tochigiken, Japan

[73] Assignee: Kabushiki Kaisha Toshiba, Kanagawaken, Japan

[21] Appl. No.: 370,176

[22] Filed: Jan. 9, 1995

[30] Foreign Application Priority Data

Jan. 11, 1994 [JP] Japan .................................. 6-001067

[51] Int. Cl.⁶ ...................................................... G01V 3/00
[52] U.S. Cl. ........................................ 324/318; 128/653.5
[58] Field of Search ...................................... 324/318, 322, 324/300, 306, 307, 309; 128/653.5

[56] References Cited

U.S. PATENT DOCUMENTS 5,154,178 10/1992 Shah ..................................... 128/653.5

Primary Examiner—Louis M. Arana
Attorney, Agent, or Firm—Limbach & Limbach L.L.P.

[57] ABSTRACT

To fix a joint portion of a patient for imaging the joint portion being bent, a joint fixing apparatus for a magnetic resonance image (MRI) system includes: a moving mechanism for bending the joint portion; and a non-magnetic driving mechanism for supplying a driving force to the moving mechanism. Further, an MRI joint imaging system for obtaining a magnetic resonance image of a joint portion of a patient by bending the joint portion includes: a moving mechanism having a fixing base for fixing the joint portion and for bending the joint portion; a non-magnetic driving mechanism for supplying a driving force to the moving mechanism; an imaging unit for imaging the joint portion; and a controller for controlling the driving mechanism and the imaging mechanism so that the bending motion of the joint portion by the driving mechanism, and the image of the joint portion by the imaging unit, can be timed with each other.

18 Claims, 12 Drawing Sheets

MRI JOINT IMAGING SYSTEM

BACKGROUND OF THE INVENTION

1. Technical Field

The present invention relates to an MRI (magnetic resonance image) joint (articulation) imaging system for imaging a joint portion of a human body (patient) by changing the bending angle thereof with the use of the MRI system.

2. Description of the Related Art

Recently, with the development of medical diagnosis systems, MRI system have been widely used. In the MRI system, a magnetic resonance image can be obtained by applying an RF pulse in a predetermined pulse sequence and an inclination magnetic field to an object to be imaged (placed in a predetermined static magnetic field) and then collecting and processing echo signals generated from the object to be imaged.

As one of the imaging techniques using the MRI system, there exists such a method where a knee joint of a patient is imaged by changing the bending angle thereof gradually so that the obtained image can be displayed as a cinematic image (motion picture). In more detail, as shown in FIG. 1, a plurality of images 1, 2 and 3 of different bending angles of the knee joint are continuously formed to obtain a cinematic image 4.

To obtain the cinematic image 4, a fixing apparatus as shown in FIG. 2 has been used so far. In the fixing apparatus shown in FIG. 2, a fixing base 8 is placed under a knee joint 7 of a patient 6 lying down on a top board 5, and the knee joint 7 is fixed to the top board 5 by use of two belts 9. That is, under the condition that the knee joint 7 is slightly bent, the knee joint 7 is covered with an RF coil 10 to obtain an MR image.

After that, the leg position of the patient 6 is moved upward by use of a leg mounting base 11 to obtain a status in which the knee joint is stretched. Under these conditions, the stretched knee joint is imaged to obtain anther MR image. When the above-mentioned imaging is repeated by changing the bending angle of the knee joint gradually, it is possible to obtain the cinematic image as shown in FIG. 1.

For the cinematic image taken based upon the conventional fixing method, however, since the operator must change the bending angle of the knee joint 7 of the patient 6 in a scanning room for each image, there exists a problem in that the operation is troublesome. In addition, since the bending angle is adjusted manually, a difference in the incremental change in angular position of the knee joint is inevitably produced between the respective images, with the result that the motion of the cinematic image is not uniform.

SUMMARY OF THE INVENTION

Accordingly, it is the object of the present invention to provide an MRI joint imaging system which can adjust the bending angle of a joint easily.

To achieve the above-mentioned object, the present invention provides a joint fixing apparatus for a magnetic resonance image system, for fixing a joint portion of a patient to image the joint portion being bent, which includes: moving means for bending the joint portion; and non-magnetic driving means for supplying a driving force to said moving means.

Further, the present invention provides an MRI joint imaging system for obtaining a magnetic resonance image of a joint portion of a patient by bending the joint portion, which includes: moving means having a fixing base for fixing the joint portion, for bending the joint portion; non-magnetic driving means for supplying a driving force to said moving means; imaging means for imaging the joint portion; and control means for controlling said driving means and said imaging means so that the bending motion of the joint portion by said driving means and image of the and joint portion by said imaging means can be timed with each other.

According to the present invention, the joint portion of a patient is bent by the non-magnetic driving means to change the bending angle of the joint portion. Therefore, whenever the driving means is rotated gradually and the joint portion is imaged to obtain a cinematic image, since any desired bending angle of the joint portion can be obtained easily without dispersion of the angular positions of the joint portion, it is possible to obtain a smooth (for instance) cinematic image.

Further, when the driving means is remote-controlled, since the operator is not required to approach the bed for changing the bending angle of the joint portion, it is possible to improve the manipulatability of the MRI equipment and thereby to reduce the imaging time.

DESCRIPTION OF THE PREFERRED EMBODIMENTS

Figure 1:
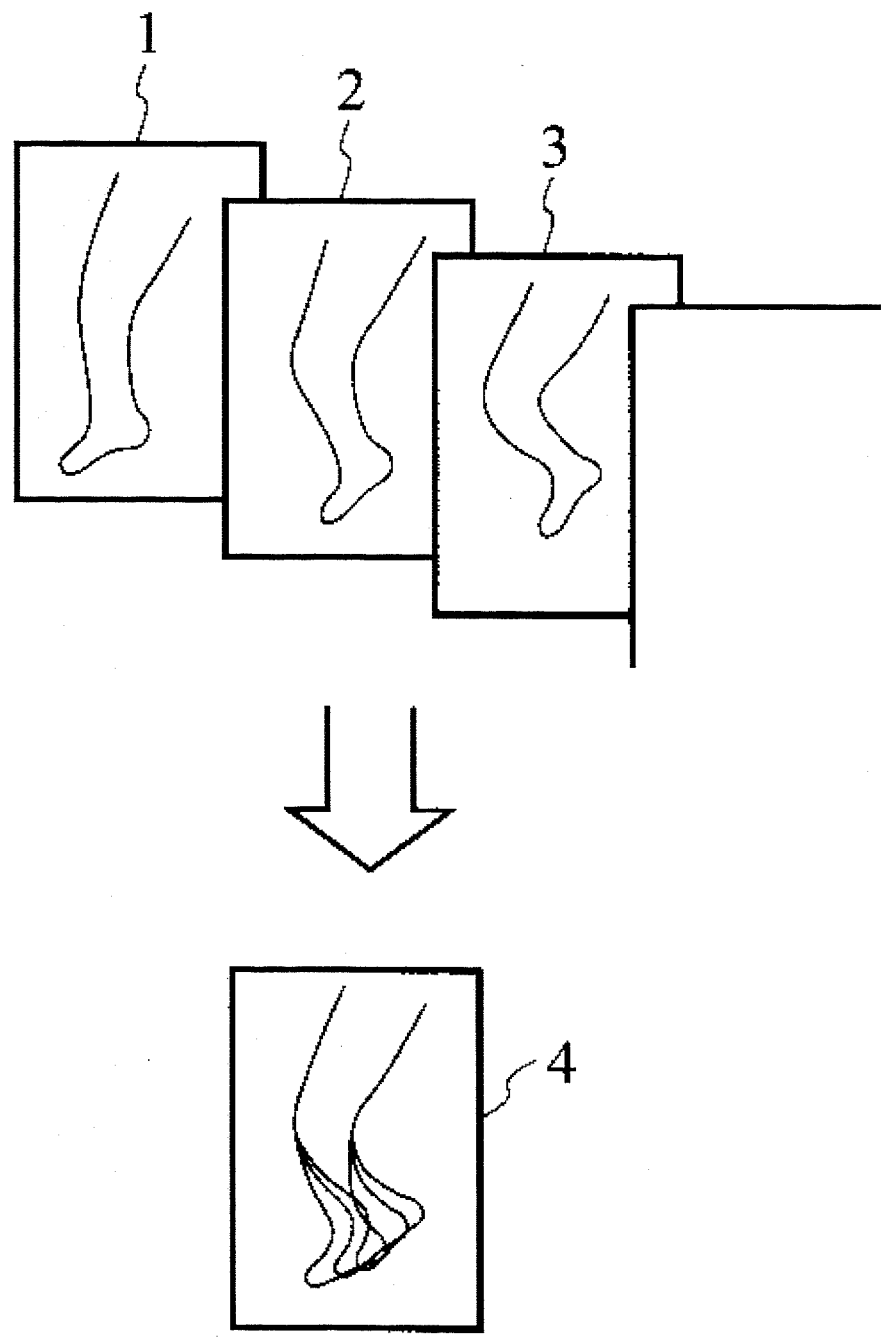
FIG. 1 is an illustration for assistance in explaining a cinematic image.
Figure 2:
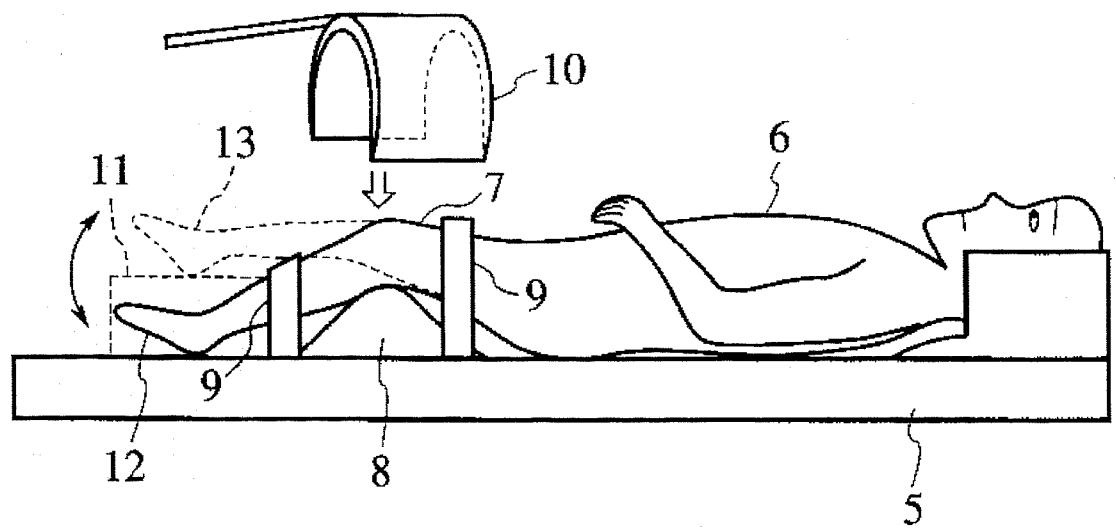
FIG. 2 is a diagrammatical view showing a prior art example of the fixing apparatus.
Figure 3:
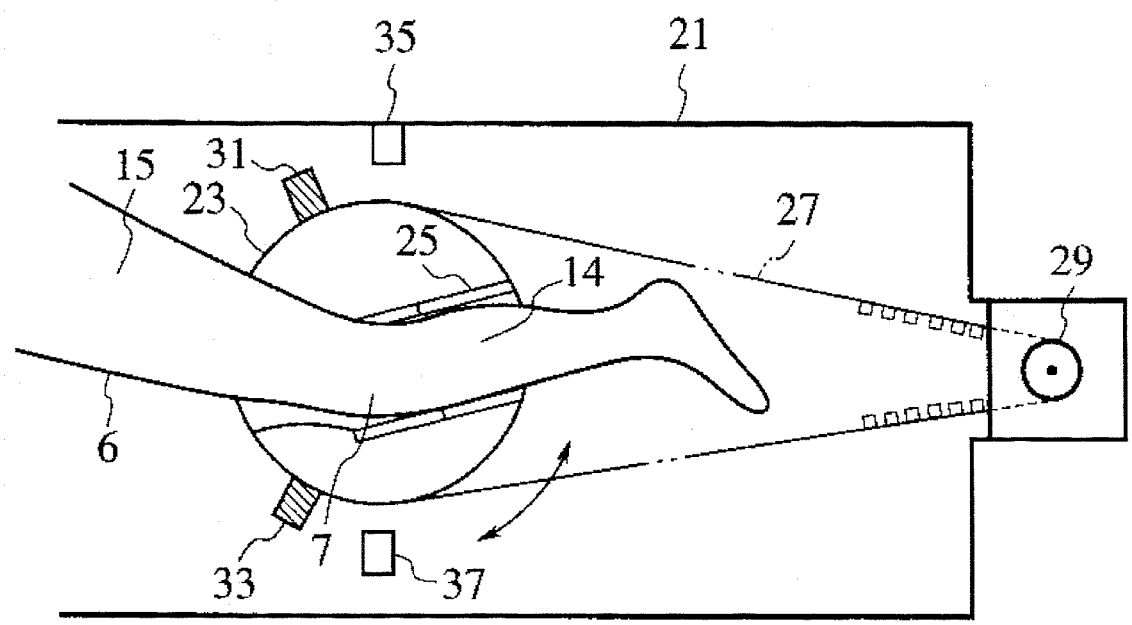
FIG. 3 is a diagrammatical view showing an embodiment of the knee joint fixing apparatus for the MRI joint imaging system according to the present invention.

The embodiments of the present invention will be described hereinbelow with reference to the attached drawings. FIG. 3 shows the knee joint fixing apparatus according to the present invention in detail, and FIG. 4 shows a block diagram of the peripheral circuits of the embodiment of the knee joint fixing apparatus for an MRI (magnetic resonance image) joint imaging system.

As shown in FIG. 3, the knee joint fixing apparatus is provided with a turntable 23 mounted on a fixing base 21. On the turntable 23, a jig 25 for fixing a leg portion 14 of a patient 6 to be inspected is disposed. The turntable 23 is connected to a non-magnetic type ultrasonic motor 29 via a timing belt 27 so as to be turned. Further, two light shading plates 31 and 33 are attached on both sides of the turntable 23; on the other hand, two photo-couplers 3S and 37 are provided so as to detect light shaded by these light shading plates 31 and 33, respectively.

In other words, the light shading plates 31 and 33 and the photo-couplers 35 and 37 constitute a limiter for controlling the turntable 23 so as not to be rotated over predetermined angular positions in either direction.

Figure 4:
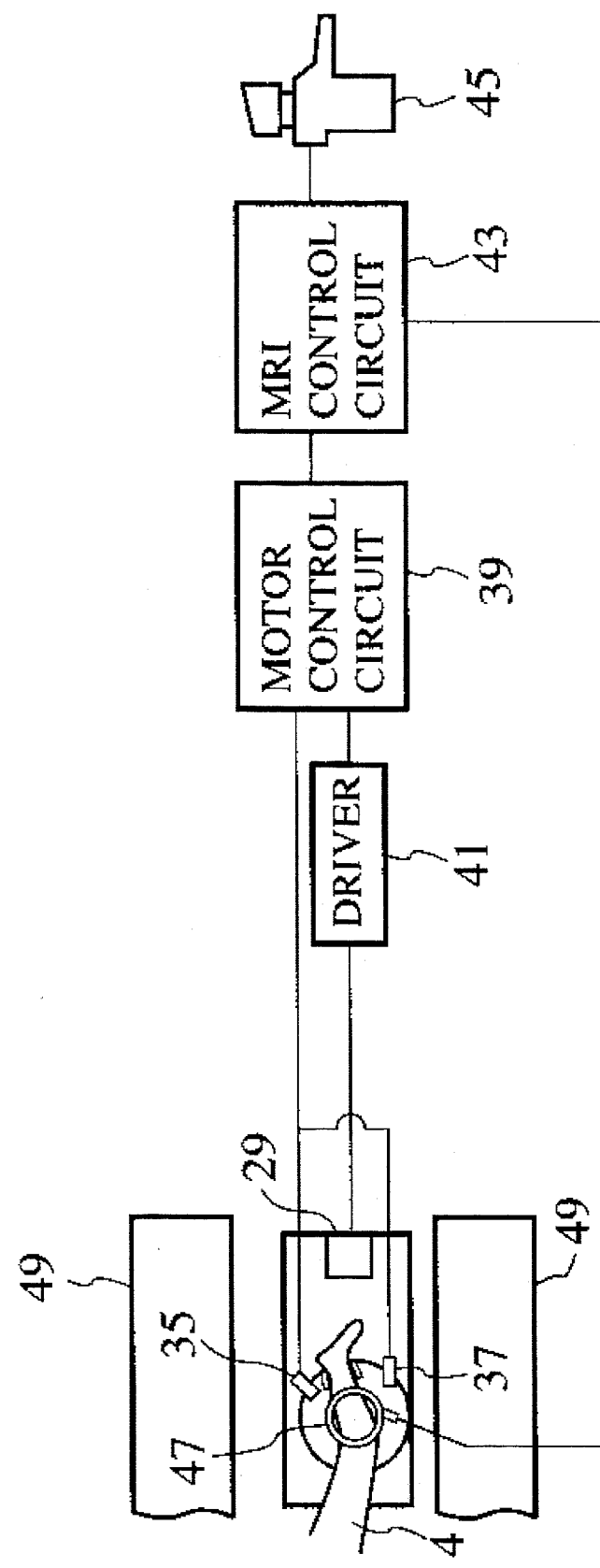
FIG. 4 is a block diagram showing the peripheral circuits of the knee joint fixing apparatus.

In more detail, in FIG. 4, the outputs of the photo-couplers 35 and 37 are applied to a motor control circuit 39 for controlling the ultrasonic motor 29. The control circuit 39 outputs a control signal to a driver 41 to control the rotation of the ultrasonic motor 29. Further, the motor control circuit 39 is activated under control of an MRI control circuit 43 for controlling an overall operation of the MRI system. Further, this MRI control circuit 43 is connected to a console 45. In addition, this MRI control circuit 43 control an RF coil 47 for imaging the knee joint 7. Further, in FIG. 4, the reference numeral 49 denotes a frame of the MRI system.

Figure 5:
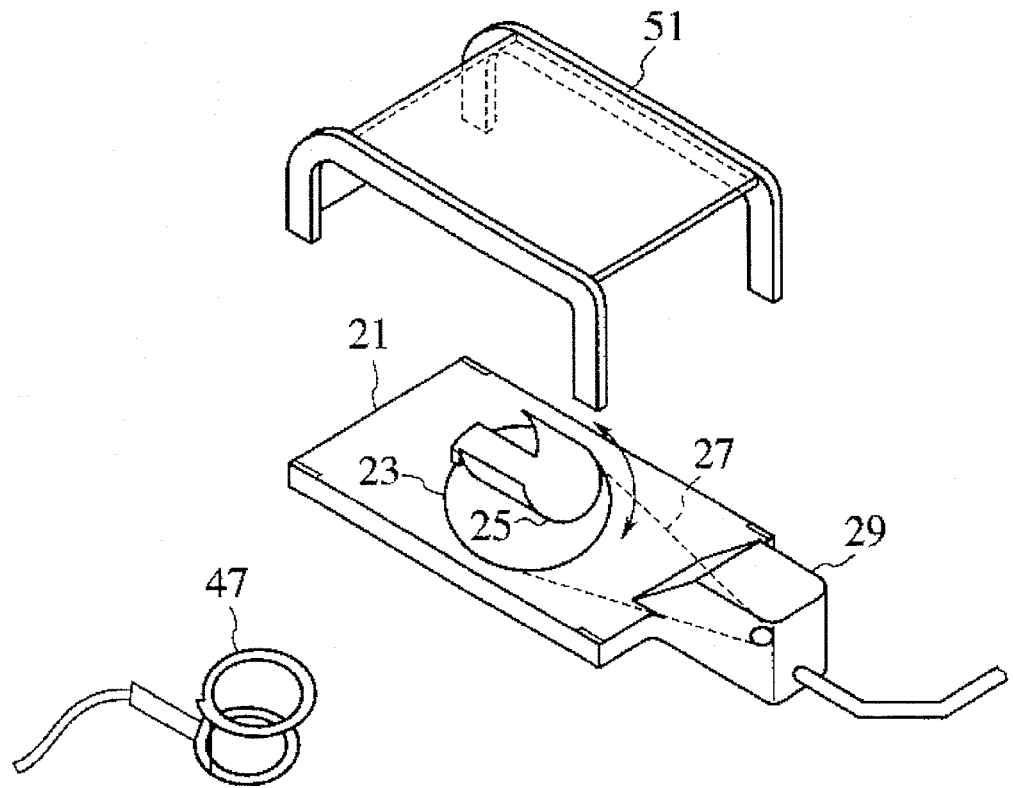
FIG. 5 is a perspective view showing the knee joint fixing apparatus according to the present invention.
Figure 6:
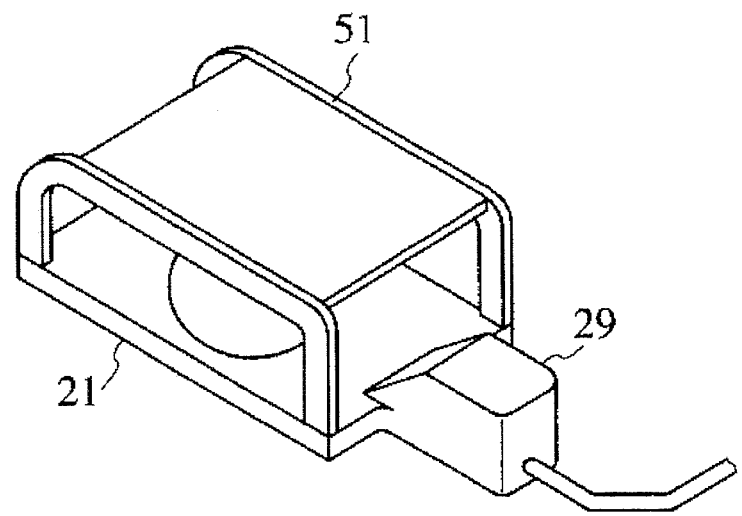
FIG. 6 is a perspective view showing an assembled knee joint fixing apparatus according to the present invention.

FIG. 5 shows an embodiment of the knee joint fixing apparatus according to the present invention, and FIG. 6 shows the assembled knee joint fixing apparatus thereof. As shown in FIG. 5, a cover 51 is attached onto the fixing base 21 so that a patient's leg fitted to jig 25 will not interfere with another leg not required to be inspected. Further, the reference numeral 47 denotes an opposing-type RF coil disposed in the vicinity of the knee joint to transmit an RF pulse and receive an echo signal reflected from the knee joint. In practical use, the knee joint fixing apparatus is so set that the fixing base 21 becomes perpendicular to a bed (not shown) of the MRI equipment.

Figure 7:
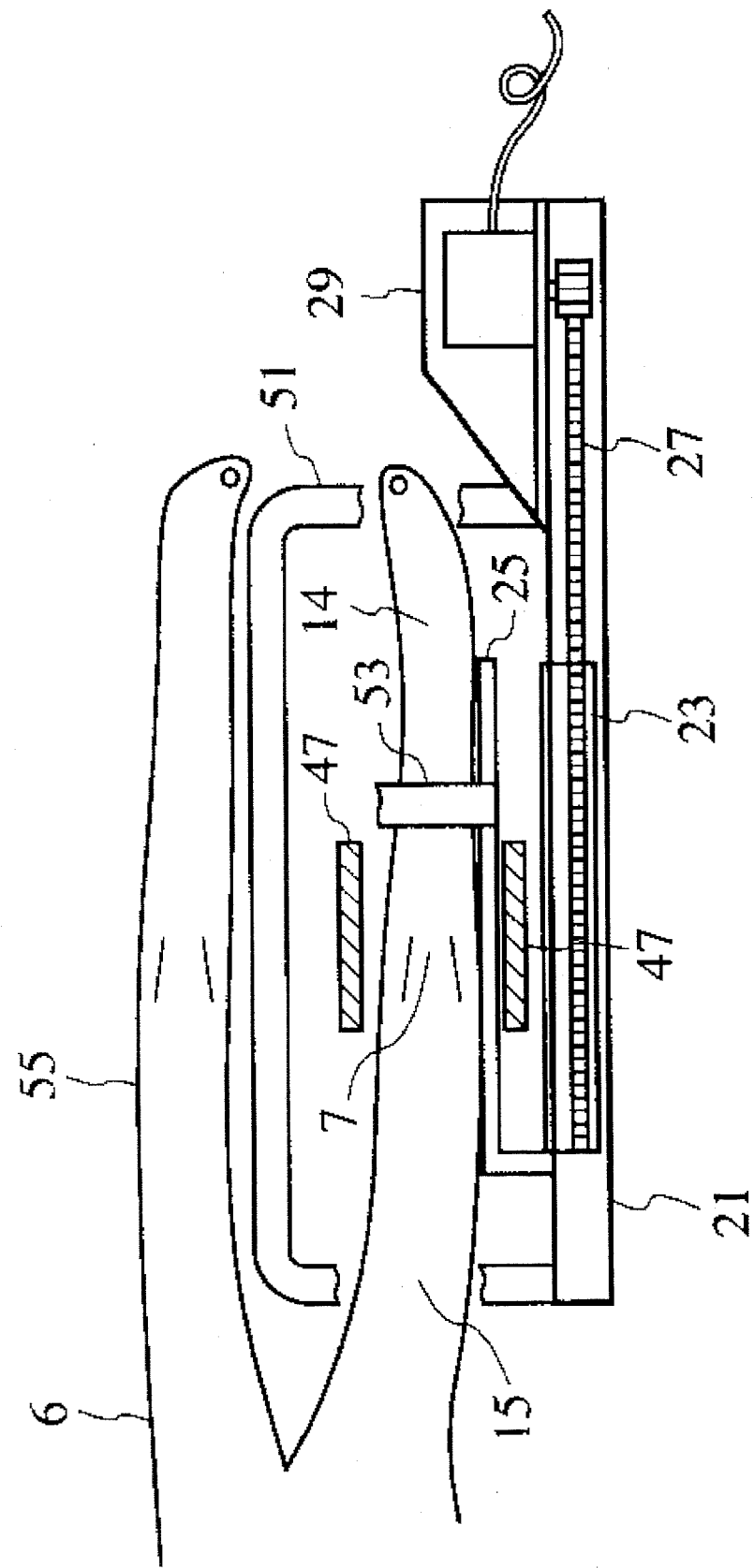
FIG. 7 is a perspective view showing the status where the knee joint fixing apparatus is attached to a patient.

FIG. 7 shows the status where the knee of a patient is set to the knee joint fixing apparatus. As shown, the leg portion 14 of the patient 6 is mounted on the jig 25 and further fixed by a fixing belt 53. The RF coil 47 is arranged so as to sandwich the knee joint 7 to obtain an MR image. Further, the leg 55 not inspected is isolated by the cover 51 so as not to interfere with the leg 14 to be inspected, as already explained.

For imaging the knee joint, the body and the femur portions 15 of a patient 6 are fixed on the fixing base 21 and further the leg portion 14 thereof is fixed by the knee joint fixing apparatus. Under these conditions, when the turntable 23 is rotated by driving the ultrasonic motor 29, the knee joint 7 can be bent at any angle, so that it is possible to obtain images of the bent knee joint 7. That is, it is possible to obtain MR images by bending the knee joint 7 gradually and thereby to obtain a cinematic image easily.

Further, since the photo-couplers 35 and 37 serve as limiters of the turntable 23 in both the directions, it is possible to prevent the turntable 23 from being rotated excessively, so that a safe operation can be achieved.

Further, since the ultrasonic motor 29 can be driven under remote control, it is unnecessary for the operator to go near the bed, thus reducing the load of the operator.

Figure 8:
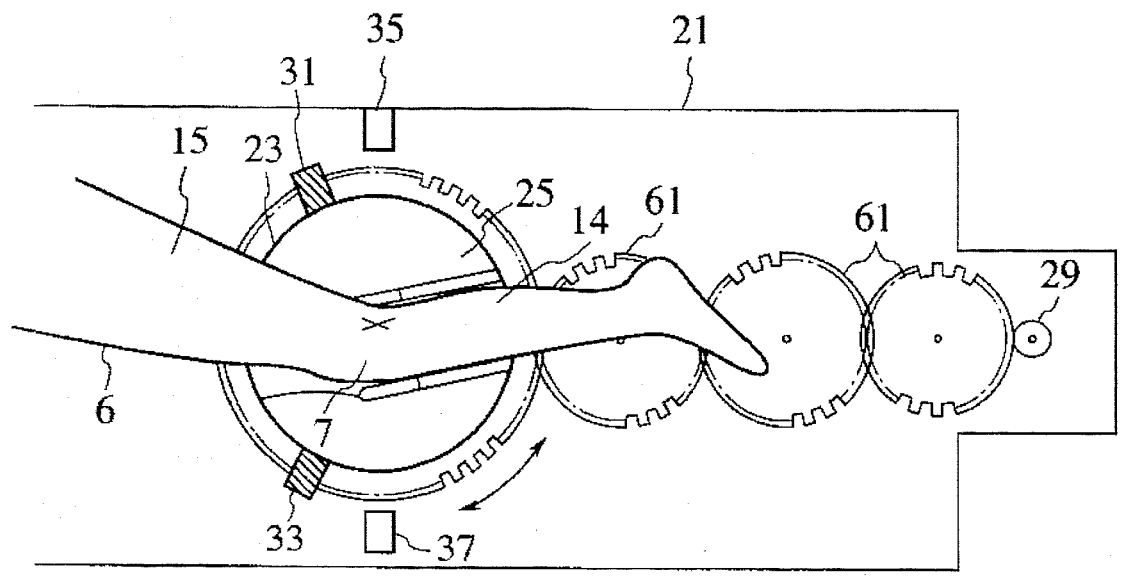
FIG. 8 is a view showing a modification in which the belt driving mechanism is replaced with a gear driving mechanism in the knee joint fixing apparatus for the MRI knee joint imaging system shown in FIG. 3.

In the above-mentioned embodiment, although the motor 29 and the turntable 23 are linked with the timing belt 27 for power transmission, without being limited only thereto, it is also possible to transmit power to the turntable 23 with the use of a gear train 61 as shown in FIG. 8.

Figure 9:
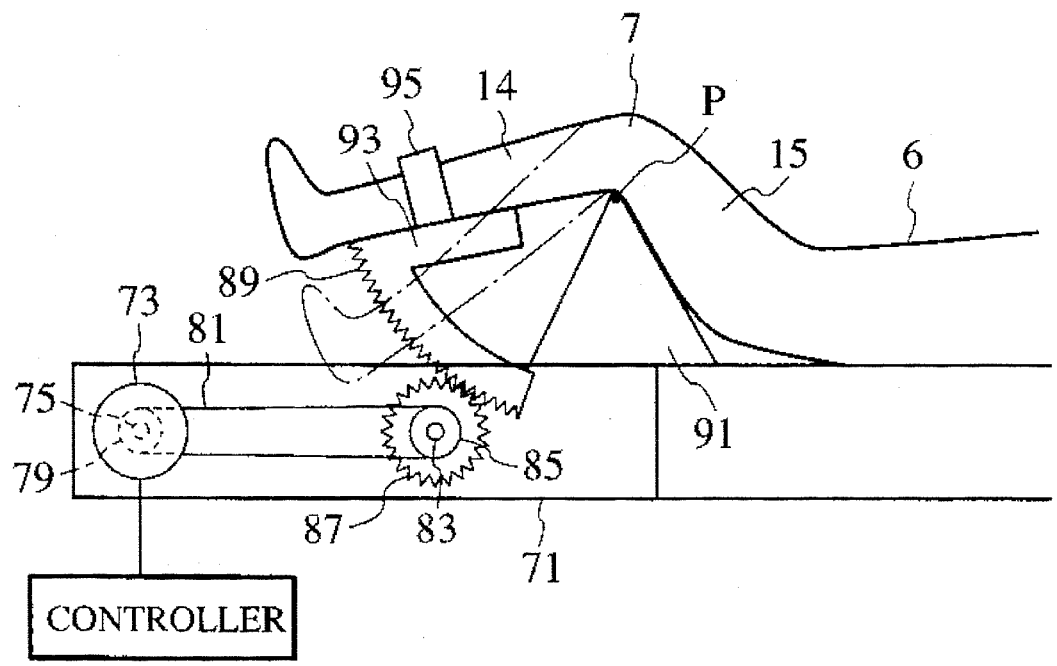
FIG. 9 is a view showing another embodiment of the knee joint fixing apparatus for the MRI knee joint imaging system according to the present invention.
Figure 10:
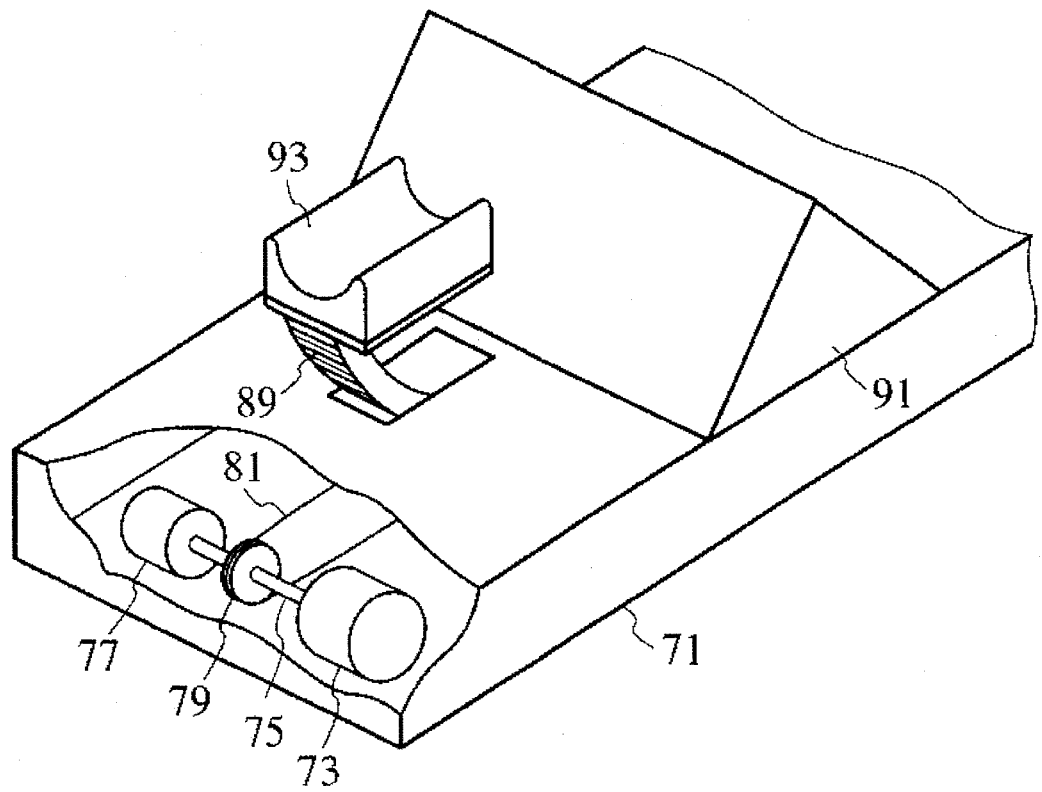
FIG. 10 is a perspective view showing the knee joint fixing apparatus for the MRI knee joint imaging system shown in FIG. 9.

FIGS. 9 and 10 show another embodiment of the knee joint fixing apparatus according to the present invention, in which the inspection can be made by setting the patient's body with his face upward.

In these drawings, a fixing base 71 is provided with a motor 73 housed therewithin. An encoder 77 is attached to an output shaft 75 of the motor 73 to detect the revolution speed and the angular position of the motor 73. Further, a pulley 79 is attached to the output shaft 75 of the motor 73. A timing belt 81 is reeved around the pulley 79. This timing belt 81 is also reeved around another pulley 85 fixed to a driven shaft 83. A pinion 87 is attached to the driven shaft 83. The pinion 87 is in mesh with a rack 89. This rack 89 is formed into a circular arc shaped with an apex P of a mat 91 (described later) as its center. A jig 93 is fixed to the rack 93 to hold the leg portion 14 of a patient 6. The mat 91 is so supported as to be pivoted about the apex P thereof. Further, a fixing belt 95 is provided for the jig 93 to fix the leg portion 14 of the patient 6. In the vicinity of the fixing jig 93, the mat 91 of triangular cross section is disposed.

The function of the knee joint fixing apparatus as described above will be explained hereinbelow. First, the patient 6 is laid down on the fixing base 71 with his face upward. Further, the lower side of his knee portion 7 is mounted on the apex P of the mat 91. Further, the leg portion 14 of the patient 6 is fixed onto the jig 93 by the fixing belt 95. Under these conditions, when the motor 73 is driven, the rotative force of the motor 73 is transmitted to the circular arc shaped rack 89 via the pulley 79, the timing belt 81, the pulley 85 and the pinion 87, so that the rack 89 is pivoted by a predetermined angle with its apex P as its center. As a result, the jig 93 is similarly pivoted with the apex P as its center, so that the leg portion 14 of the patient 6 (fixed by the jig by the fixing belt 95) can be pivoted by a predetermined angle relative to his femur portion 15.

Figure 11:
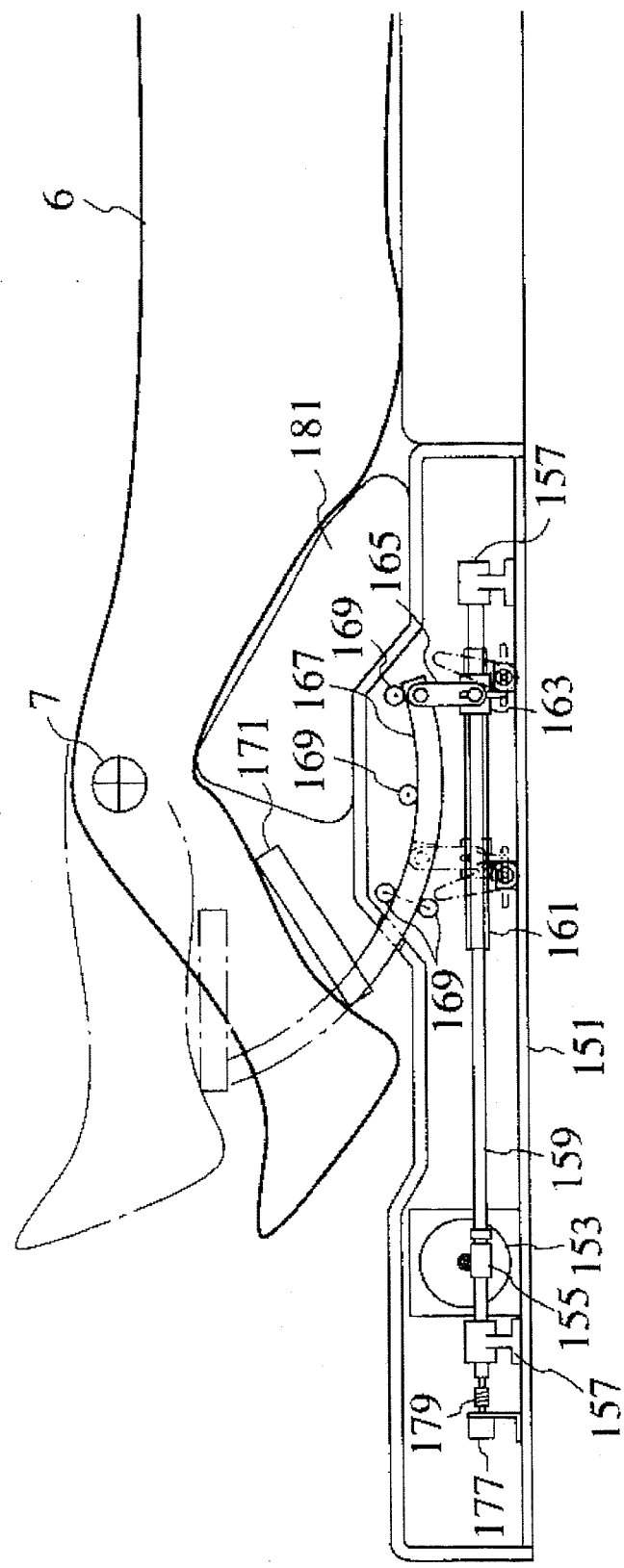
FIG. 11 is still another embodiment of the knee joint fixing apparatus for the MRI knee joint imaging system according to the present invention.
Figure 12:
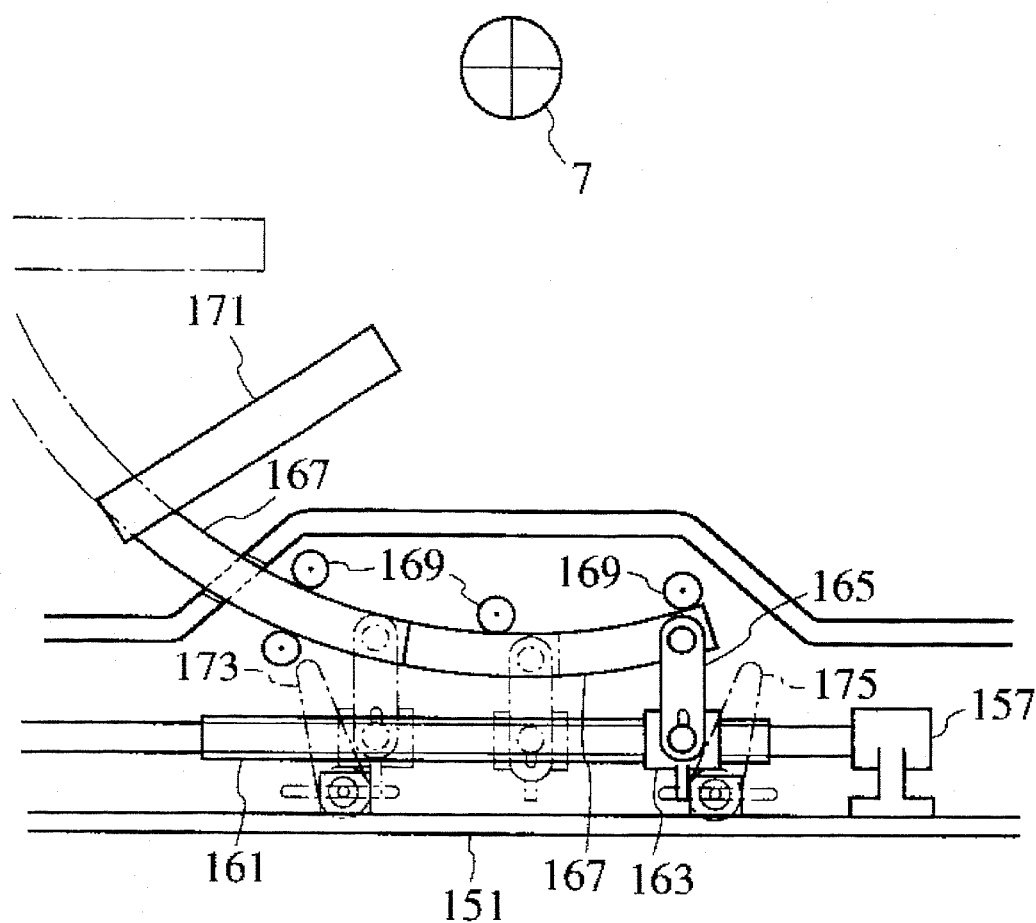
FIG. 12 is an enlarged view showing the middle portion of the knee joint fixing apparatus shown in FIG. 11.
Figure 13:
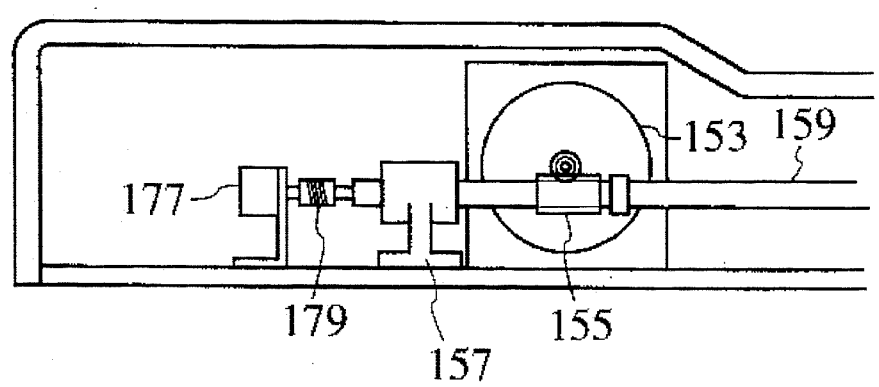
FIG. 13 is an enlarged view showing the front end portion of the knee joint fixing apparatus shown in FIG. 11.

FIGS. 11 to 13 shows still another embodiment of the knee joint fixing apparatus according to the present invention. In this embodiment, a motor 153 is provided in the fixing base 151. The revolution of the motor 153 is transmitted to a spindle 159 supported by a bearing 157 via a worm gear 155, so that a lead screw 161 formed in this spindle 159 can be rotated. A female thread portion 163 linked with a link 165 is in mesh with this lead screw 161. The link 165 is connected to a rail 167 formed into a circular arc shaped with the knee portion 7 of the patient 6 as its center. The circular arc shaped fall 167 is guided by guide rollers 169 so as to be pivoted with the knee portion 7 of the patient 6 as its center in the same way. A jig 171 is provided on the upper end of the circular arc shaped rail 167 to fix an ankle of the patient 6.

Further, in FIG. 12, the reference numeral 173 denotes an upper limit mechanical stopper, and 175 denotes a lower limit mechanical stopper. Both stoppers 173 and 175 serve to limit the oscillation range of the circular arc shaped rail 167. Further, in FIG. 13, the reference numeral 177 denotes an encoder attached to the spindle 159 via a coupling 179 to detect the rotation of the spindle 159, that is, an oscillation angle of the jig 171.

Further, a mat 181 is mounted on the fixing base 151, and the leg of the patient 6 is mounted on this mat 181.

In the construction as described above, when the motor 153 is rotated, since the spindle 159 and the lead screw 161 are both rotated through the worm gear 155, the female thread portion 163 is shifted in the horizontal direction. As a result, the circular arc shaped rail 167 and the jig 171 are both pivoted about the knee portion 7 of the patient 6, so that the patient's knee is bent at a predetermined angle.

Figure 14:
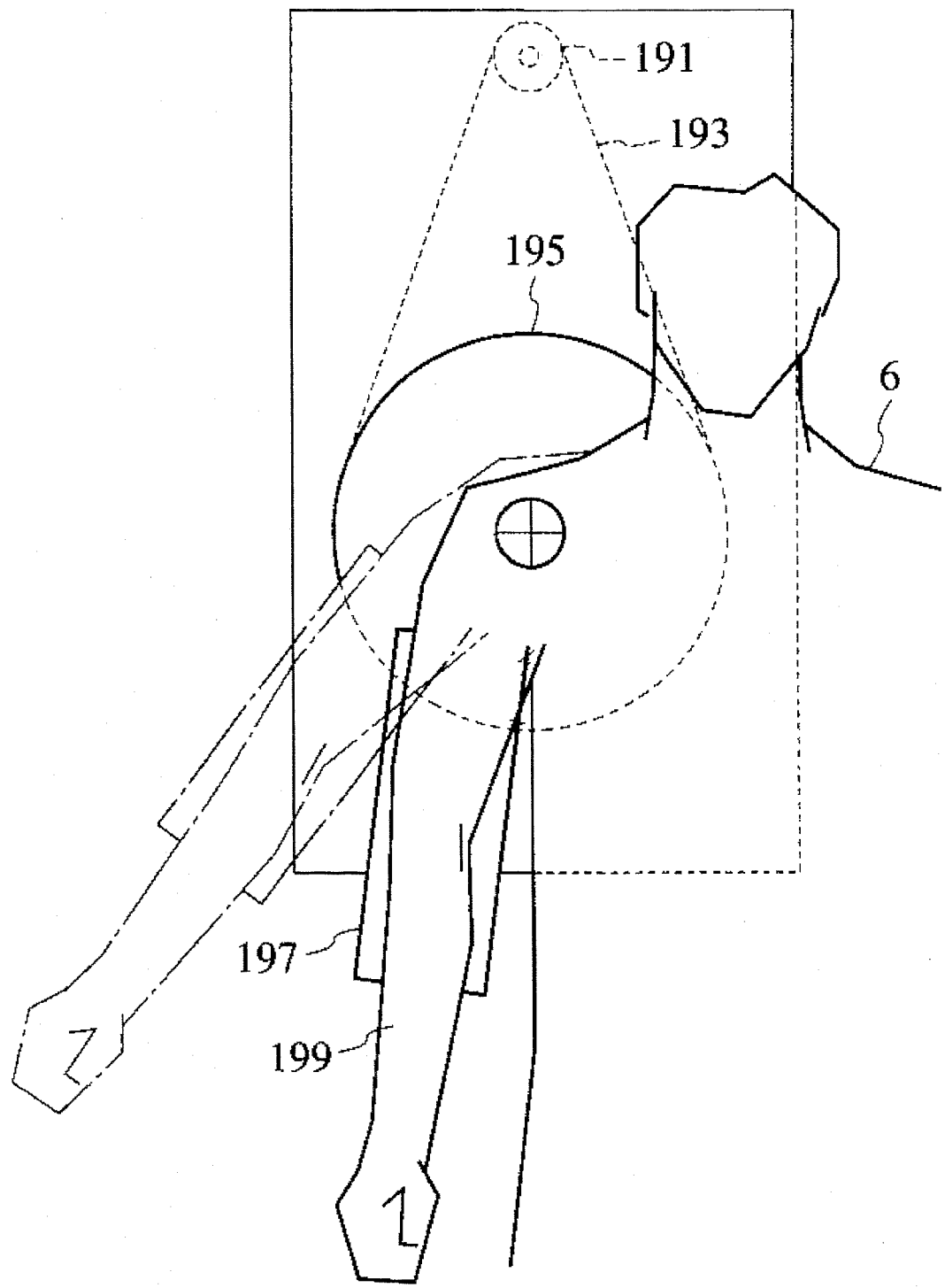
FIG. 14 is an embodiment in which the joint fixing apparatus for the MRI knee joint imaging system according to the present invention is applied to fix a shoulder joint.

FIG. 14 shows another embodiment according to the present invention, in which the knee joint fixing apparatus according to the present invention is applied to a shoulder joint. In the fixing apparatus, the rotation of a motor 191 is transmitted to a turntable 195 via a timing belt 193. The turntable 195 is provided with a jig 197 to fix an arm 199 of a patient 6. When the turntable 195 is rotated, it is possible to hold the arm 199 at any desired angle.

As described above, without being limited to only the knee joint, the joint fixing apparatus according to the present invention can be applied to various joints such as elbow joint, neck joint, hip joint, etc.

Figure 15:
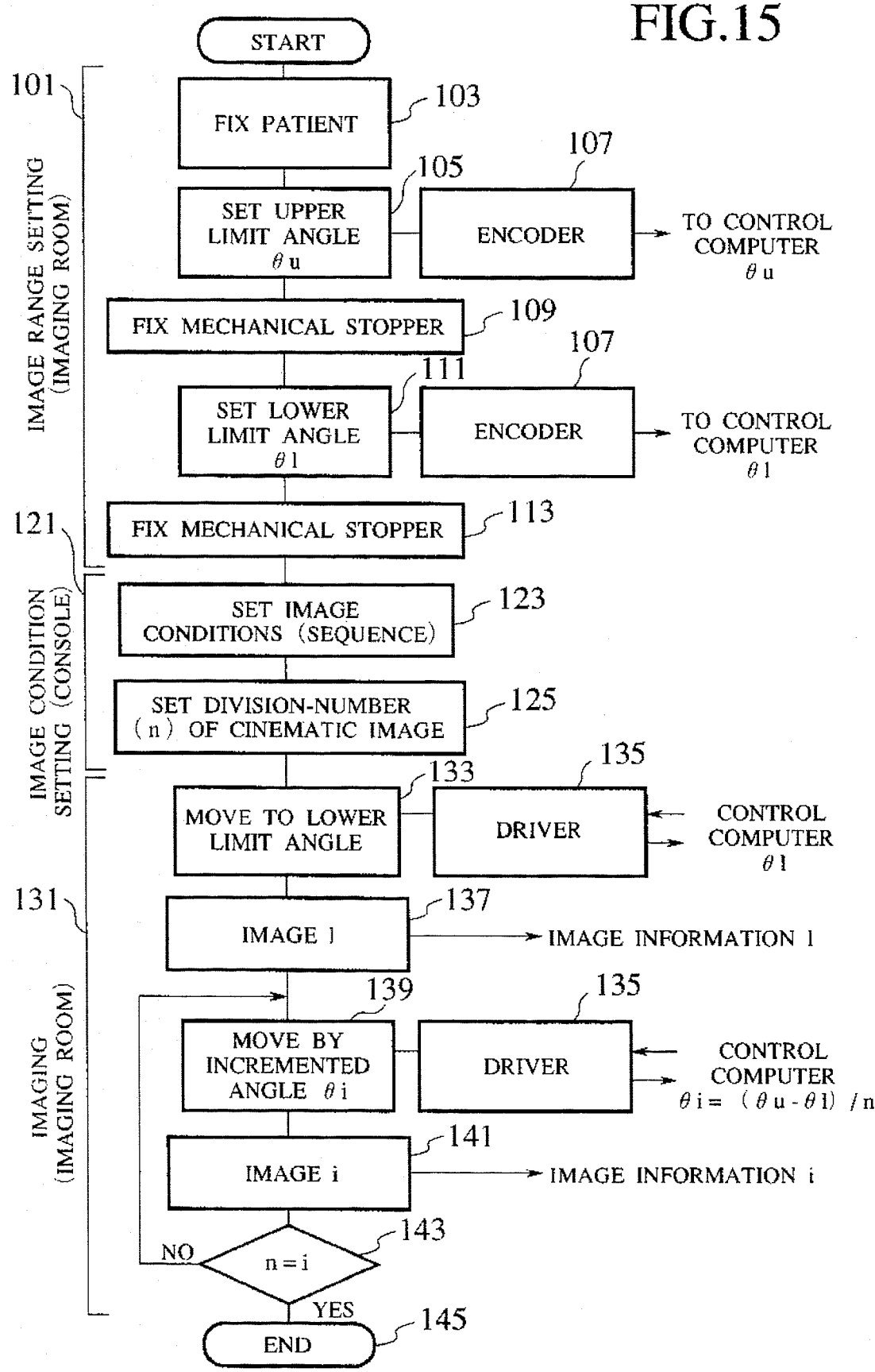
FIG. 15 is a flowchart showing the imaging procedure of the MRI joint imaging system according to the present invention.

With reference to FIG. 15, the method of imaging a joint by use of the MRI joint imaging system using the above-mentioned fixing apparatus will be described. In FIG. 15, a reference numeral 101 denotes an imaged range setting procedure effected within an image room. First, in step 103, a patient is fixed. After that, in step 105, an upper angle $\downarrow u$ of the knee to be imaged is set. This set angle is transmitted to a control computer via an encoder 107. Further, in step 109, the mechanical stopper for limiting the upper limit angle is fixed. After that, in step 111, the lower limit angle $\downarrow l$ of the knee to be imaged is set. This set angle $\downarrow l$ is transmitted to a control computer via the encoder 107. Further, in step 113, the mechanical stopper for limiting the lower limit angle is fixed.

A reference numeral 121 denotes a image condition setting procedure by use of the console. First, in step 123, the image conditions (sequence) are set. Then, in step 125, the number n of the divided cinematic images is set.

A reference numeral 131 denotes a image procedure. First, in step 133, the jig is moved to the lower limit angle $\downarrow l$. The lower limit angle $\downarrow l$ is transferred between the jig and the control computer through a driver 135, then this incremented angle $\downarrow l$ is transmitted to a control computer via the encoder. After that, in step 137, a joint is imaged for the first time. By this first image 1, the first image information 1 can be obtained. Further, in step 139, the jig is moved by an increment angle $\downarrow i$. The incremented angle $\downarrow i$ is transferred between the jig and the control computer through the driver 135, then this incremented angle $\downarrow i$ is transmitted to a control computer via the encoder. Here, $$\Theta i = (\Theta u - \Theta l)/n.$$

After that, in step 141, the same joint is imaged. By this image i, the image information 1 can be obtained. Further, in step 143, it is discriminated whether n=i can be established. If n is i, in step 145, all the procedure ends. If n is not yet i, the procedure returns to step 139 to repeat the similar imaging procedure.

In the above-mentioned embodiments, the knee joint fixing apparatus has been mainly explained by way of example. However, without being limited only thereto, the joint fixing apparatus according to the present invention can be applied to various joint portions (e.g., elbow, neck, hip, etc.). In this case, the fixing belt and the bending angle direction are appropriately modified.

Further, in the above-mentioned embodiments, the joint portion has been imaged only when kept at a halt. However, without being limited only thereto, it is possible to image the joint in motion. In this case, the timing of the image sequence and the timing of the joint bending angle are to be controlled appropriately.

As described above, in the joint fixing apparatus according to the present invention, since the joint of a patient is bent by use of non-magnetic driving means, a high precision bending angle setting apparatus can be realized, with the result that it is possible to obtain a cinematic image of smooth motion, for instance.

Further, since the joint bending angle can be changed under remote control, the operator's labor can be reduced, and further there exists such an effect that the imaging time can be reduced.

What is claimed is:

1. A joint fixing apparatus for a magnetic resonance image system that images one of two knee joint portions of a patient, which comprises:

moving means for fixing and bending the one knee joint portion to be imaged;

means for supporting the other of the knee joint portion not being imaged so as to not interfere with the one knee joint portion; and non-magnetic driving means for supplying a driving force to said moving means.

2. The joint fixing apparatus according to claim 1, wherein said driving means comprises a power source and transmitting means for transmitting power of the power source to said moving means.

3. The joint fixing apparatus according to claim 2, wherein the power source is an ultrasonic motor.

4. The joint fixing apparatus according to claim 3, wherein said moving means includes:

a disk-shaped turntable; and a jig disposed on said turntable, for holding a part connected to the one knee joint portion.

5. The joint fixing apparatus according to claim 3, wherein said power transmitting means is a timing belt.

6. The joint fixing apparatus according to claim 3, wherein said power transmitting means is a gear train.

7. The joint fixing apparatus according to claim 1, wherein said driving means is remote-controlled.

8. An MRI joint imaging system for obtaining magnetic resonance image of a joint portion of one of the knees of a patient by bending the joint portion, which comprises:

moving means having a fixing base for fixing and bending the joint portion of the one knee;

means for supporting the other of the knees not being imaged so as to not interfere with the one knee joint portion being bent;

non-magnetic driving means for supplying a driving force to said moving means;

imaging means for imaging the joint portion of the one knee; and control means for controlling said driving means and said imaging means so that the bending motion of the joint portion of the one knee by said driving means, and the image of the joint portion of the one knee by said imaging means, can be timed with each other.

9. The joint fixing apparatus according to claim 7, further comprising:

a limiter means for limiting the range of the bending of the one knee joint portion.

10. The joint fixing apparatus according to claim 8, further comprising:

a limiter means for limiting the range of the bending of the joint portion of the one knee.

11. A joint fixing apparatus for a magnetic resonance image system that images one of two knee joint portions of a patient, which comprises:

a fixing base for supporting the patient by his/her back;

moving means attached to the fixing base for bending the one knee joint portion to be imaged, said moving means having a movable member which supports the back of the one knee joint portion and which is pivotable about an axis of rotation of the one knee joint portion; and non-magnetic driving means for supplying a driving force to said moving means.

12. The joint fixing apparatus according to claim 11, wherein said driving means comprises a power source and transmitting means for transmitting power of the power source to said moving means.

13. The joint fixing apparatus according to claim 12, wherein the power source is an ultrasonic motor.

14. The joint fixing apparatus according to claim 13, wherein said power transmitting means is a timing belt.

15. The joint fixing apparatus according to claim 11, wherein said driving means is remote-controlled.

16. The joint fixing apparatus according to claim 13, wherein said driving means is remote-controlled.

17. The joint fixing apparatus according to claim 16, further comprising:

a limiter means for limiting the range of the bending of the one knee joint portion.

18. An MRI joint imaging system for obtaining a magnetic resonance image of a joint portion of one of the knees of a patient by bending the joint portion, which comprises:

a fixing base for supporting the patient by his/her back;

moving means attached to the fixing base for bending the one knee joint portion to be imaged, said moving means having a movable member which supports the back of the one knee joint portion and which is pivotable about an axis of rotation of the one knee joint portion;

non-magnetic driving means for supplying a driving force to said moving means;

imaging means for imaging the one knee joint portion; and control means for controlling said driving means and said imaging means so that the bending motion of the one knee joint portion by said driving means, and the image of the one knee joint portion by said imaging means, can be timed with each other.

* * * * *